US006217529B1

(12) United States Patent
Wax et al.

(10) Patent No.: US 6,217,529 B1
(45) Date of Patent: Apr. 17, 2001

(54) PUBOCOCCYGEAL TRAINING BIOFEEDBACK DEVICE

(75) Inventors: Michael S. Wax; Michel A. Boileau; Gary L. Hoffman; Matthew W. Hoskins, all of Bend, OR (US); William G. McCoy, Spokane, WA (US); William E. Clem; Robert Mesaros, both of Bozeman, MT (US)

(73) Assignee: Deschutes Medical Products, Inc., Bend, OR (US)

( * ) Notice: Subject to any disclaimer, the term of this patent is extended or adjusted under 35 U.S.C. 154(b) by 0 days.

(21) Appl. No.: 09/563,102

(22) Filed: May 2, 2000

Related U.S. Application Data

(63) Continuation of application No. 09/007,122, filed on Jan. 14, 1998, now Pat. No. 6,063,045.
(60) Provisional application No. 60/068,470, filed on Dec. 3, 1997.

(51) Int. Cl.[7] ............................. A61B 5/103; A63B 23/20
(52) U.S. Cl. .............................. 600/591; 482/8; 482/112; 482/113; 600/587; 73/379.01; 606/192
(58) Field of Search ................................. 600/29, 30, 31, 600/587, 591; 606/191, 192, 193, 197; 601/23, 148, 149, 150; 482/111, 112, 113; 128/830, 834, 836, 885, 898; 73/379.01–379.09

(56) References Cited

U.S. PATENT DOCUMENTS

| 577,775 | 2/1897 | Mussey | 606/192 |
|---|---|---|---|
| 1,413,789 | 4/1922 | Schaff | 606/192 |
| 2,507,858 | 5/1950 | Kegel | 600/591 |

(List continued on next page.)

FOREIGN PATENT DOCUMENTS 41 39 241 A1   5/1993 (DE).

OTHER PUBLICATIONS

InCare brochure dated 1992.
Jacques G. Susset, et al., "Biofeedback Therapy for Female Incontinence Due to Low Urethral Resistance," *Journal of Urology*, vol. 143, pp. 1205–1208 (Jun. 1990).
Jacques G. Susset, "Perineal Reeducation: Treatment for Incontinence," *InCare Medical Products*, (1989).

*Primary Examiner*—Cary O'Connor
*Assistant Examiner*—Charles Marmor, II
(74) *Attorney, Agent, or Firm*—Klarquist Sparkman Campbell Leigh & Whinston, LLP

(57) ABSTRACT

A training device is disclosed for exercising the pubococcygeal or pelvic floor muscles, for example in the treatment of incontinence. The device includes a cylindrical, deformable probe for insertion into the vagina or rectum of a user. The probe is connected to a pressure transducer, which detects the pressure applied to the probe by contraction of the pelvic floor muscles and displays a pressure indicator to the user to help direct the contraction of the appropriate muscles. The pressure indicator may take the form of a series of nested figures, such as curves or concentric semi-circles, that incrementally converge toward a common point as pressure on the probe increases. The nested figures incrementally retreat from the common point as pressure on the probe decreases. The training unit guides a user through an exercise routine by tracking the overall exercise time and the timing between flexing and relaxation cycles. The training unit can include a controller, such as a microcontroller, that is coupled to the inflatable probe for detecting the pressure within the probe. The controller tracks the timing of exercises performed by the user and guides the user through alternating cycles of muscular contraction and relaxation to provide a safe and effective biofeedback regimen.

24 Claims, 10 Drawing Sheets

U.S. PATENT DOCUMENTS

| | | | |
|---|---|---|---|
| 2,541,520 | 2/1951 | Kegel | 600/591 |
| 3,726,273 * | 4/1973 | Cole | 600/591 |
| 3,916,906 | 11/1975 | Gerry | 606/192 |
| 3,933,147 | 1/1976 | Du Vall | 600/591 |
| 4,050,449 | 9/1977 | Castellana | 128/2 |
| 4,167,938 | 9/1979 | Remih | 600/591 |
| 4,216,783 * | 8/1980 | Kaiser et al. | 600/591 |
| 4,396,019 * | 8/1983 | Perry, Jr. | 600/546 |
| 4,515,167 | 5/1985 | Hochman | 600/549 |
| 4,873,990 | 10/1989 | Holmes et al. | 600/561 |
| 4,909,263 | 3/1990 | Norris | 607/39 |
| 5,005,586 | 4/1991 | Lahr | 600/587 |
| 5,154,177 | 10/1992 | Eisman et al. | 600/373 |
| 5,167,237 | 12/1992 | Rabin et al. | 600/561 |
| 5,483,832 | 1/1996 | Pauser et al. | 73/379.08 |
| 5,674,238 | 10/1997 | Sample | 606/192 |
| 5,733,230 | 3/1998 | Sawchuck et al. | 482/111 |
| 6,086,549 * | 7/2000 | Neese et al. | 600/587 |

* cited by examiner

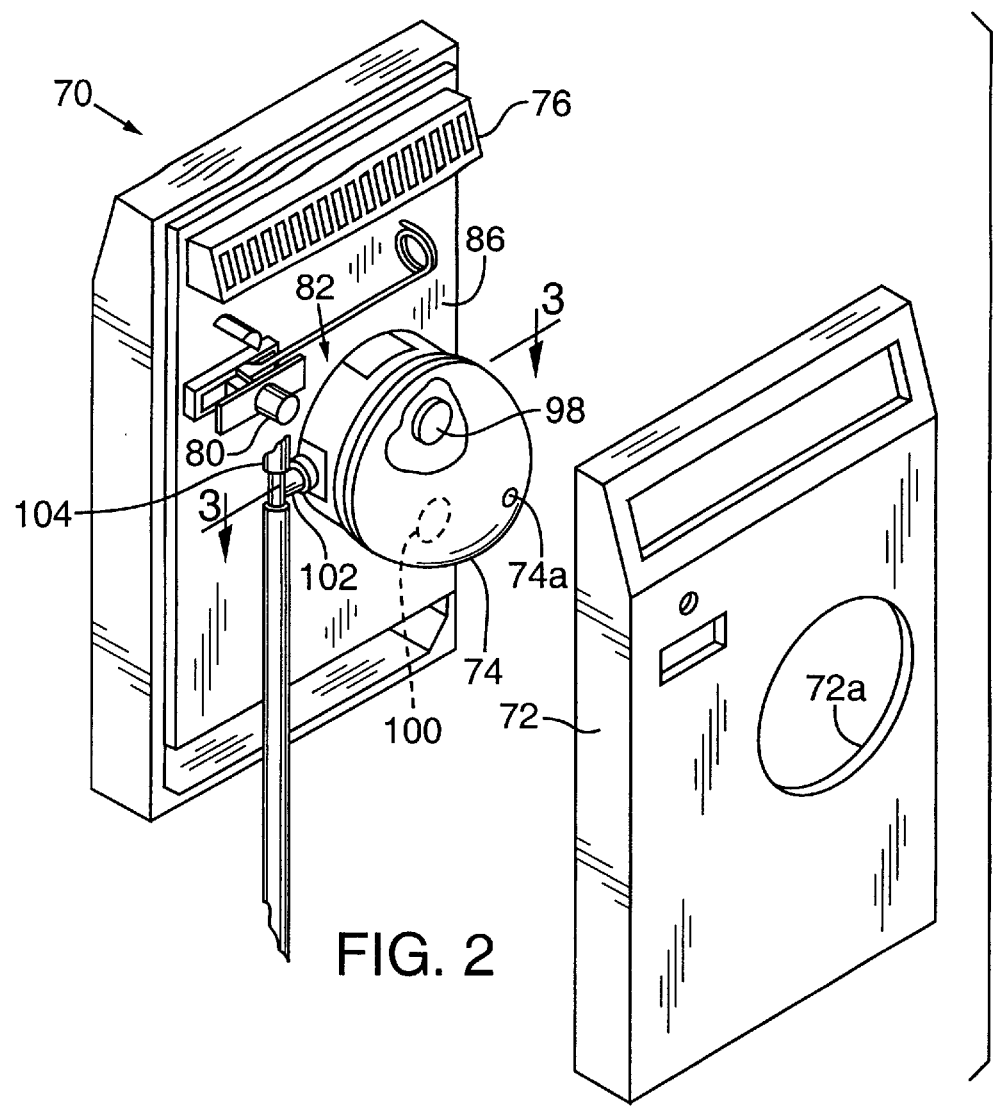
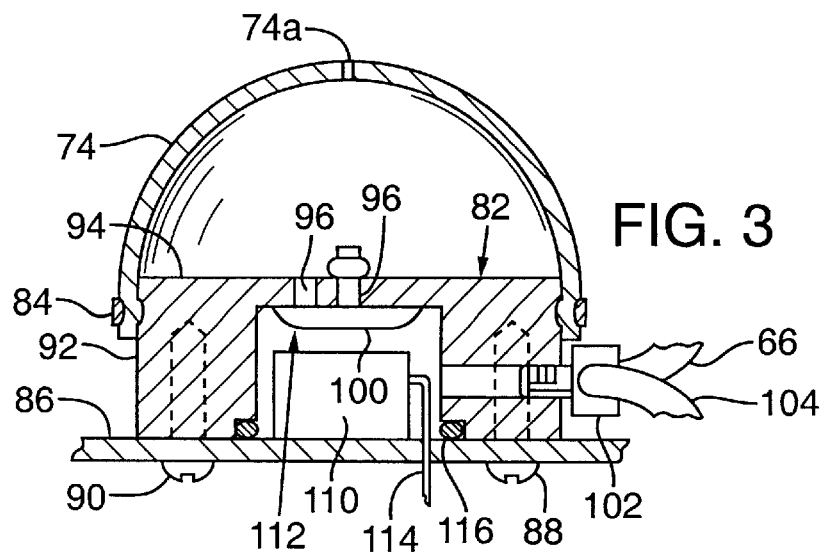

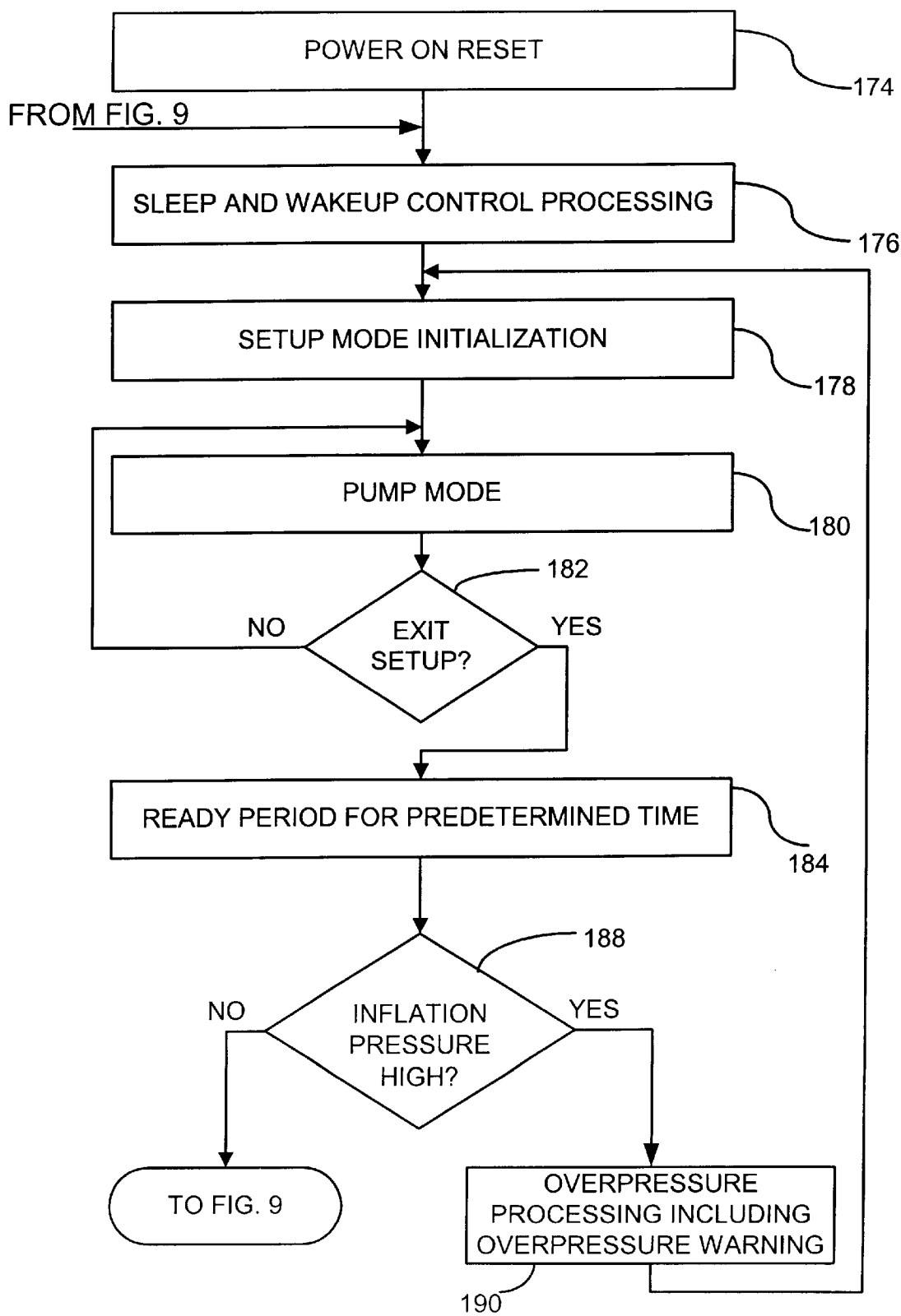

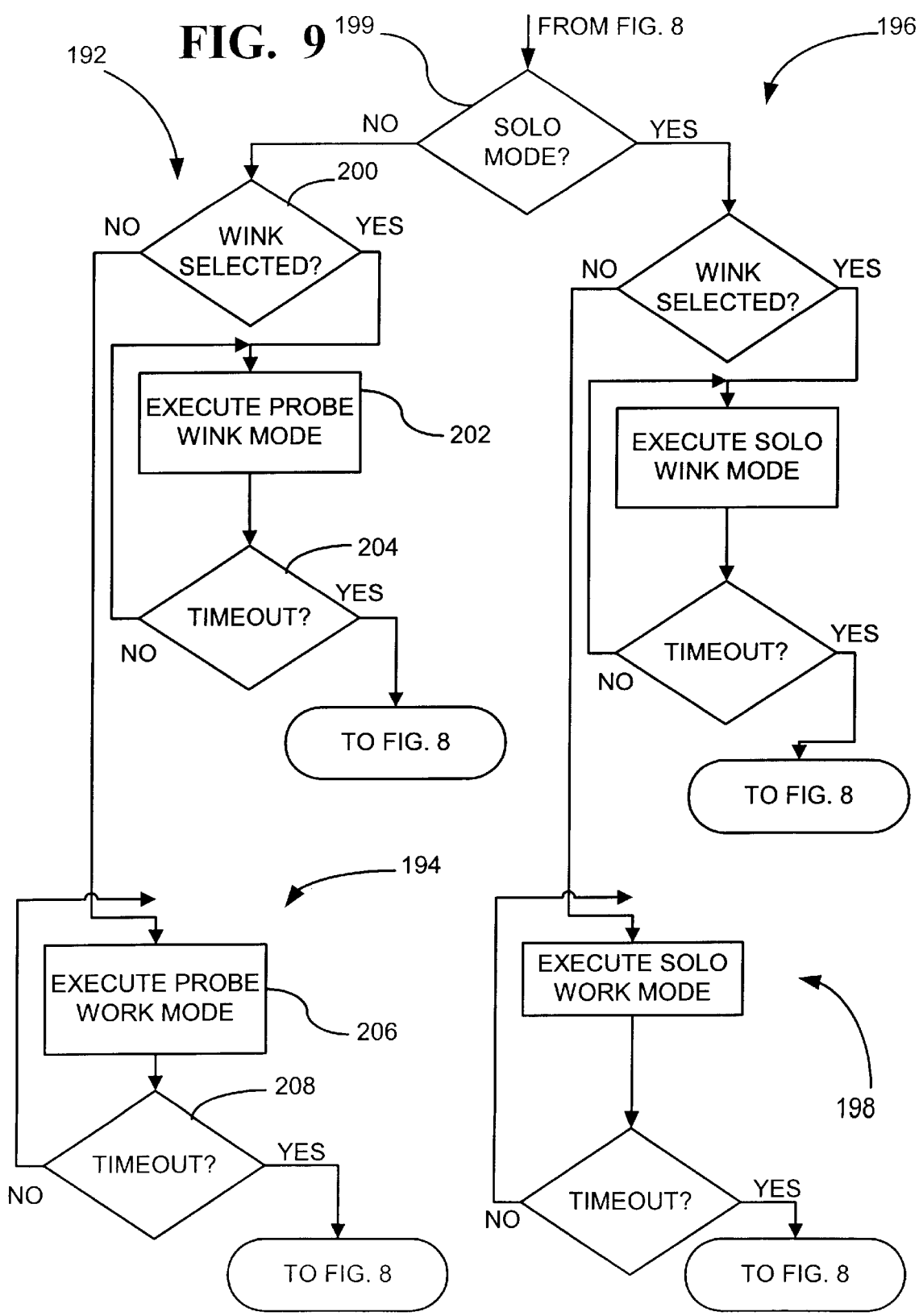

PROBE OR SOLO WORK MODE

PROBE OR SOLO WINK MODE

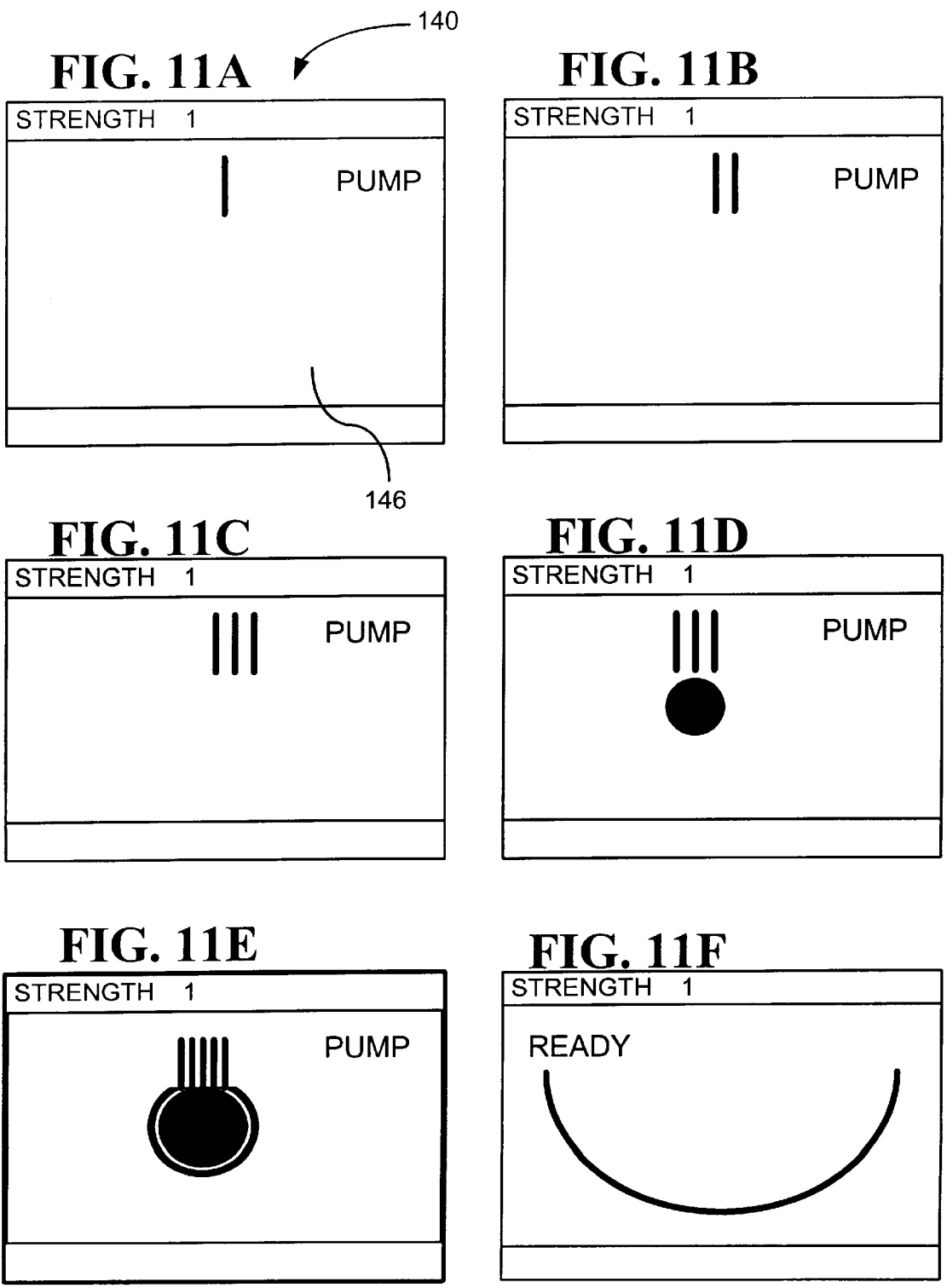

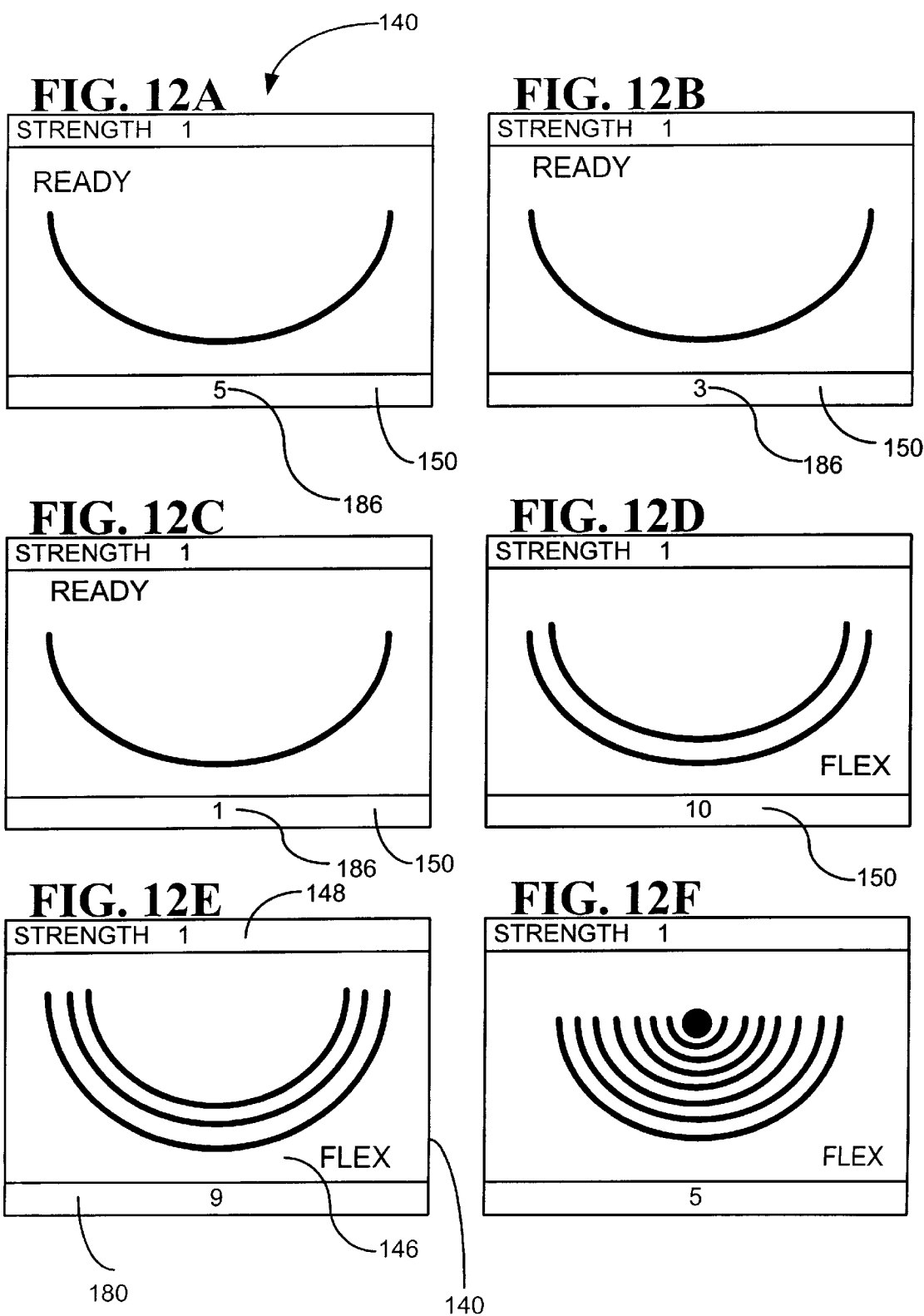

PUBOCOCCYGEAL TRAINING BIOFEEDBACK DEVICE

RELATED APPLICATION DATA

This Application claims the benefit of U.S. patent application Ser. No. 09/007,122 filed Jan. 14, 1998, now U.S. Pat. No. 6,063,045, which claims the benefit of U.S. Provisional Patent Application No. 60/068,470 filed on Dec. 3, 1997.

FIELD OF THE INVENTION

The present invention relates generally to an apparatus for strengthening the pubococcygeal muscles (i.e., pelvic floor muscles) for improved sphincter or urinary control, and improving erectile dysfunction. More particularly, this invention relates to a biofeedback device that guides a user through an exercise program for the pelvic floor muscles.

BACKGROUND OF THE INVENTION

Over 18 million people in the US suffer from urinary incontinence. Many forms of incontinence have been linked to poor muscle tone in the pubococcygeus or pelvic floor muscles. The pelvic floor muscles originate from the symphysis pubis and extend posteriorly encompassing the urethra, the vagina, and the rectum. The pelvic floor muscles often work in conjunction with other muscles, such as the sphincter urethrae, to control urination. Many pathological conditions, such as cystocoel (hernial protrusion of the urinary bladder through the vaginal wall), rectocoel (hernial protrusion of part of the rectum into the vagina), uterine prolapse (protrusion of the uterus through the vaginal orifice), and bladder and sexual dysfunctions, may be caused by a weakened condition of the pelvic floor muscles. It is widely known that treatment of these pathological conditions generally includes development of muscle tone in the pelvic floor muscles.

One procedure for improving tone in the pelvic floor muscles is for the patient to exercise these muscles through voluntary contractions. Many patients find it difficult to perform such exercises because of an unfamiliarity with how to control the pelvic floor muscles or due to the weakened state of the muscles. Some types of voluntary exercises have been prescribed, such as the exercises developed by Dr. Arnold Kegel. To perform these exercises properly requires instruction, such as the insertion of an instructor's finger into the vagina or anus to determine when the correct muscles have been contracted. Once the patient has learned to contract the correct muscle group, the patient repeats the contractions many times per day. The requirement for personal instruction is often an impediment to a patient seeking care for incontinence or other conditions caused by pelvic muscular dysfunction.

Many training devices have therefore been developed for assistance in exercising the pelvic floor muscles. For example, U.S. Pat. No. 4,167,938 to Remih discloses a vaginal muscle exerciser having an inflatable, compressible body connected to an air cell. The air cell houses a piston connected to a tongue which raises and lowers a U-shaped pointer riding along a numerical scale to indicate the pressure. As a user applies pressure to the body by contraction of the pelvic muscles, air is forced out of the body, through a tube and into the air cell. As air enters or leaves the air cell, the piston moves upwardly or downwardly to approximately indicate on the scale the amount of applied pressure. A digital readout of the total pressure applied to the compressible body is also disclosed.

U.S. Pat. No. 2,541,520 to Kegel discloses another device for exercising injured sphincter muscles. The device includes a resilient member that is inserted within a sphincter muscle. A hose connects the device to a mechanical pressure gauge and an externally located pump. As pressure is applied to the inflatable member by the user's sphincter muscles, air is forced from the resilient member, through the hose and toward the mechanical pressure gauge, where the pressure is approximately indicated by a needle on the pressure gauge.

None of these prior devices, however, have been able to provide a fully effective exercise regimen.

SUMMARY OF THE INVENTION

The present invention has taken advantage of the recognition of several previously unappreciated drawbacks of the prior art. Although both Remih and Kegel provide devices for exercising the pelvic floor muscles, they do not guide the user through the exercises. For example, the present inventors have found that a drawback of the prior devices is that they do not direct a user when to flex the pelvic floor muscles and for how long. Additionally, these prior devices do not prevent the user from over-inflating or under-inflating the inflatable member, nor did they recognize that under-inflation reduces the effectiveness of the exercises. Furthermore, the pressure gauges of these prior devices show the total pressure in the inflatable member, rather than increased pressure due to contraction of the pelvic floor muscles. The present inventors have also found that users have difficulty judging contractile strength based on the readout of the calibrated pressure gauges. The analog and digital displays are difficult for a user to correlate with the subjective experience of the contraction.

The present invention has overcome these previously unappreciated problems, by providing a device having embodiments which present an intuitively helpful display to the user that more effectively correlates with the subjective sensations associated with pelvic floor muscle contractions. The intuitive display may for example be a series of arcs, concentric rings, or portions of concentric rings, that mimic the tightening of the muscles of the pelvic floor around a probe inserted in the vagina or rectum. The number, color, or brightness of the concentric rings or arcs may increase or decrease to signify tightening or loosening of the pubococcygeal muscles. Some embodiments of the invention also function as training devices that guide a user through an exercise routine, detect and correct improper or injurious pressurization of an inflatable probe, detect subtle contractile pressures, and/or have a central pump bladder and display.

In particular embodiments, the present invention includes a biofeedback training unit for exercising the pelvic floor muscles by guiding a user through an exercise routine. The training unit tracks the overall exercise time and the time between flexing and relaxation cycles. The training unit also monitors pressure in a probe to ensure the pressure remains within predetermined limits. If an error is detected due to improper pressure, the training unit automatically prompts the user to take corrective action.

In one aspect of the invention, the training unit includes an inflatable, elongated, cylindrical probe for insertion into an orifice such as the vagina or rectum. The probe is a sensitively designed balloon sensor that adjusts to the user's anatomy. Additionally, the probe's pneumatic design ensures that electrical components are not placed in the user's body. The training unit houses a controller, such as a microcontroller or microprocessor, which is coupled to the inflatable probe for detecting the pressure in the probe. A display is coupled to the controller and includes a pressure indicator portion that displays information associated with the contraction and relaxation of the user's pelvic floor muscles. The pressure indicator portion displays the pressure increase due to contraction of the pelvic floor muscles, rather than a total pressure within the probe. Displaying the pressure increase due to muscle contraction allows the user to accurately assess muscle strength. The controller also tracks the timing of the exercises and guides the user through alternating flexing and relaxation cycles to provide a safe and effective urinary control regimen.

In another aspect of the invention, the controller monitors the pressure and determines whether the pressure is above or below a predetermined threshold. If a pressure problem is detected, the controller automatically takes corrective action. For example, if the pressure is below a predetermined limit, the controller automatically terminates the workout cycle and advises the user to increase the pressure in the probe. If the pressure is above a predetermined limit, the controller automatically warns the user and suspends further exercises until the pressure decreases.

These and other features of the present invention will be more readily apparent from the following detailed description of a preferred embodiment which proceeds with reference to the accompanying drawings.

BRIEF DESCRIPTION OF THE DRAWINGS

FIG. 2 is an exploded perspective view of the control/display unit of FIG. 1.

FIG. 3 is an enlarged view taken along line 3—3 in FIG. 2.

FIG. 8 is a flowchart of steps taken by the training unit of FIG. 7 prior to entering a workout phase.

FIG. 9 is a top-level flowchart of steps taken by the training unit of FIG. 7 after entering a workout phase.

FIGS. 11A–11F are illustrations of information displayed on the training unit of FIG. 7 prior to entering a workout phase.

FIGS. 12A–12F are illustrations of information displayed on the training unit of FIG. 7 prior to and during a workout phase.

DETAILED DESCRIPTION OF THE PREFERRED EMBODIMENTS

Figure 1:
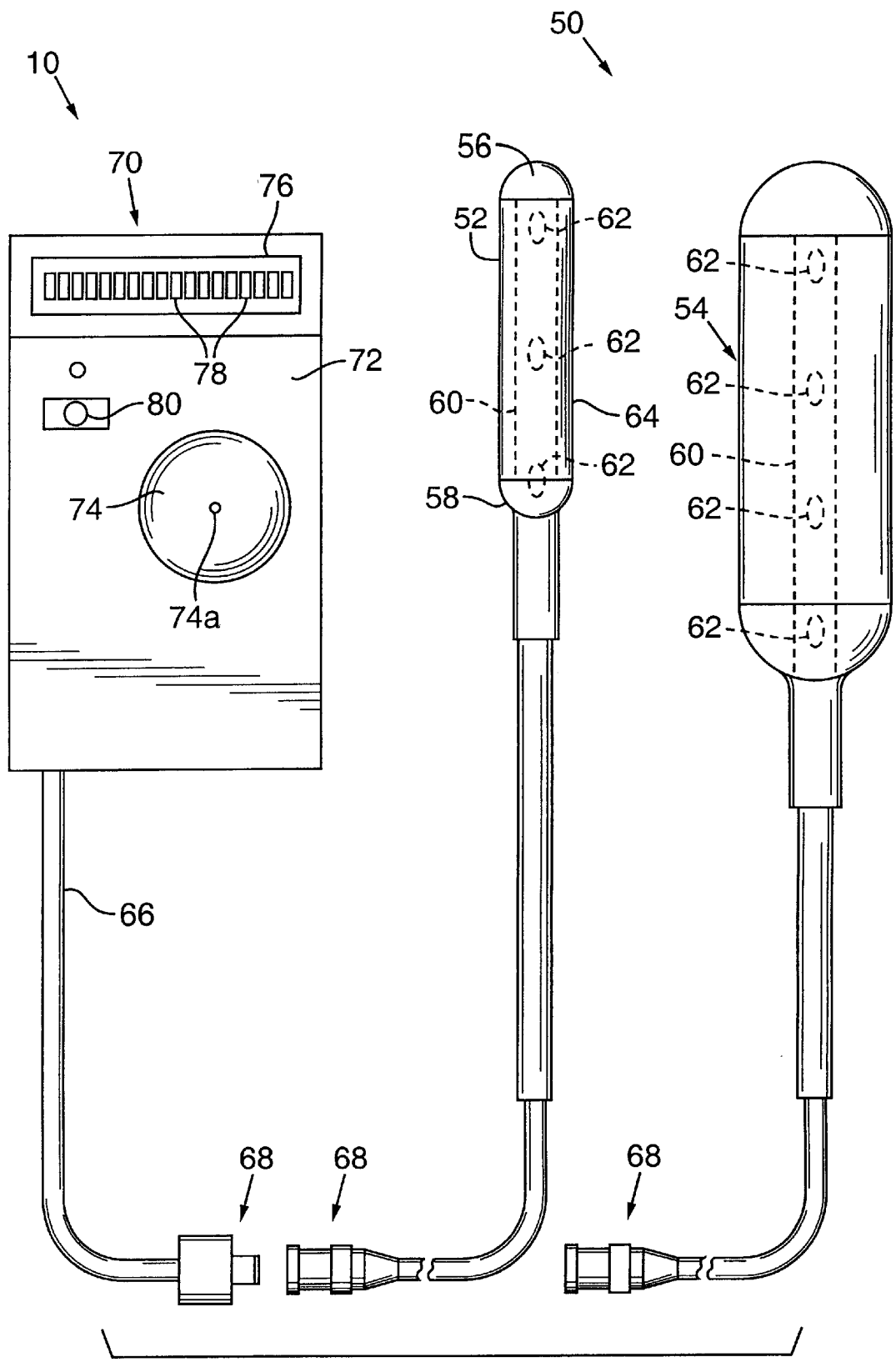
FIG. 1 is a view of a first embodiment of a training unit that includes a control/display unit in association with a rectal and a vaginal probe.

FIG. 1 shows a first embodiment of the pubococcygeal muscular contraction sensing and feedback display apparatus 10, for enabling a user to strengthen the pelvic floor muscles through biofeedback, in a way which will be described in more detail below. The user can be, for example, someone suffering from any condition associated with weakness of the muscles of the pelvic floor. Persons who have urinary stress incontinence are an example (without limitation) of a population of users that would benefit from use of the device. However, the apparatus 10 could also be used for any other condition that would benefit from exercising the pelvic floor muscles.

Apparatus 10 includes an inflatable probe 50, which is insertable into an orifice of the user. A male subject would use a relatively smaller probe 52, which is designed for insertion into the anus, with the tip residing in the rectum. A female subject would use a slightly larger probe 54 which is designed for insertion through the vaginal opening for retention in the vagina. Because each probe is substantially the same except for the orifice in which its use is intended, only probe 52 will be described, it being understood that probe 54 is similarly constructed.

Figure 5:
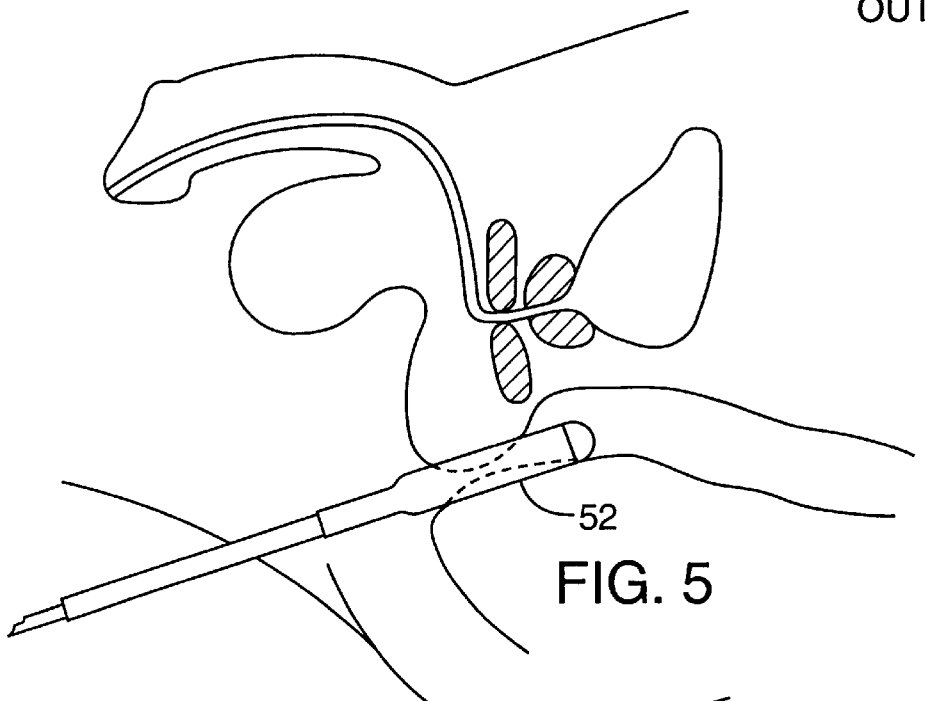
FIG. 5 is a schematic cross-sectional view showing the rectal probe in use in a male subject.

As shown in FIGS. 1 and 5, probe 52 is preferably elongated and includes hemispherical end caps 56, 58 of molded plastic. A hollow, tubular structure 60 extends between caps 56, 58, and a series of openings 62 extend through the tube. Caps 56, 58 and tubular structure 60 are enveloped by any suitable non-toxic, elastic, heat shrink skin 64 suitable for use in the human body. A central, compressible portion of probe 52 (between caps 56, 58) is yieldable in response to contraction and relaxation of the user's muscles, as described in more detail below. The probes 50 are in effect a specially designed balloon sensor that adjusts to individual patient anatomy. Additionally, the probes' pneumatic design allows the probe to be used without placing electrical components in the user's body.

A tube-like conduit 66 is attached at one end to the probe 50, and at its other end to a control/display unit 70. The conduit 66 may be interrupted, for example, by a male/female coupling joint 68, so that the probe 50 and unit 70 can be selectively disconnected. The conduit serves an air conveying function described in more detail below.

The control/display unit 70 (FIGS. 1 and 2) attached to one end of conduit 66 includes a housing, having a top face 72, a pump bladder 74 operatively connected to conduit 66 for inflating probes 52, 54, and a user-visible display 76 for providing biofeedback to the user. Preferably, bladder 74 is made of any suitable shape-retentive elastomeric material which is resiliently reboundable, and display 76 is electronically controllable by electronic componentry located inside unit 70 and described in more detail below. Display 76 includes multiple, light-emitting diodes (LEDs) 78 forming a substantially linear array, generally in the form of a bar-graph type display. An on/off switch 80 controls the electronic componentry described above and is movable between three different settings or power ranges which include an easy, medium, and advanced setting for allowing the user to define and vary the strenuousness of the exercises.

As shown in FIGS. 2 and 3, bladder 74 may be mounted on a manifold 82 by a circular clamping member 84, and the manifold in turn is fixed on a board 86 inside unit 70. The bladder is generally hemispherically shaped and includes a central aperture 74a. When housing face 72 is in place, bladder 74 extends through an aperture 72a in housing face 72 so as to be accessible by the user. It will be appreciated that the reboundable characteristics of bladder 74 are due to its elastomeric construction, which also makes it yieldable in response to digital pressure applied by a user, as described in more detail below.

FIG. 3 shows manifold 82 mounted on board 86 with screws 88, 90. Manifold 82 includes a cylindrical wall portion 92 having a flat bottom face abutting wall portion 92, and a top flat face 94. Apertures 96 pass through flat face 94 to enable check valves 98 (FIG. 2) and 100 (FIG. 3) to pass therethrough, for a purpose described in more detail below. A standard T-joint connector 102 is connected between manifold 82 and conduits 66, 104.

A pressure-sensing transducer 110 (FIG. 3), also called a sensor, is mounted within a cavity 112, within manifold 82, and includes electrical contact structure 114 which couples the transducer between probe 50 and display 76. An O-ring 116 provides an air-tight seal for accurate transducer operation.

Figure 4:
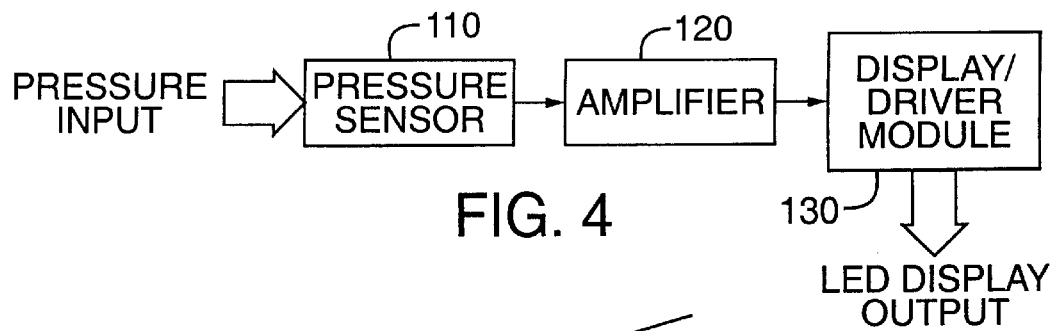
FIG. 4 is a block diagram schematically illustrating the electrical components within the control/display unit of FIG. 1.

A simplified diagram of the electrical system of the current invention is shown in FIG. 4. The pressure sensor 110, which senses and determines pressure input generated by compression of the central compressible portions of the probe 50, converts the sensed pressure into a representative signal which is conveyed to display/driver module 130 after suitable amplification by amplifier 120. The display/driver module 130 includes the LED-formed array 78. The specific components to implement the electrical system just described will be understood by those of skill in the art. However, in the illustrated embodiment, transducer 110 is the Sensyn packaged probe SX05D element, which operates well in pressure ranges of between 0 to 5 psi, although any suitable transducer will do. The illustrated embodiment also uses the LM358 dual operational amplifier package manufactured by National Semiconductor as amplifier 120, and two TSM2934 LED arrays may be used for the display/driver module. On/off switch 80 (FIG. 1) is a STS2400PC slide switch suitably coupled between the power supply (which may be AA batteries, not shown) and module 130 in a manner which will be understood by those of skill in the art. To complete the electrical system, a suitable resistor network (not shown) is added for an offset adjust.

Embodiment of FIGS. 7–13

A second embodiment of the training unit is shown in FIGS. 7–13. The probe 50 can be essentially the same as shown in FIGS. 1–6, but the training unit that receives pressure signals and provides feedback to the user is different. As particularly shown in FIG. 13, a training unit 130 includes an outer case 132 for housing a printed circuit board 134. As shown in the side view FIG. 13B, a lid 136 is rotatably mounted to the outer case 132 by a hinge 138. The top view of FIG. 13A shows the lid 136 in the closed position wherein the lid 136 protects the user interface components, including a display 140, user input buttons 142 and a pump bladder 144. The display 140 is a liquid crystal display (LCD) having a pressure indicator portion 146, a strength or scale portion 148, and a timing portion 150, each of which will be described more fully below. The training unit 130 guides a user through an exercise routine that includes alternating cycles wherein the user flexes and then relaxes their pelvic floor muscles.

The user input buttons 142 include a power on/off button 152, a strength button 154, a solo button 156 and a time button 158. The power on/off button 152 turns the training unit on and off. The strength button 154 changes a scale setting of the pressure indicator portion 146 of the display 140. The solo button 156 places the training unit 130 in solo or probe mode wherein the probe 50 can be disabled or enabled, respectively. The time button 158 changes the duration of the flexing and relaxation cycles. The pump bladder 144 is similar to that shown and described in FIG. 3.

Figure 13A:
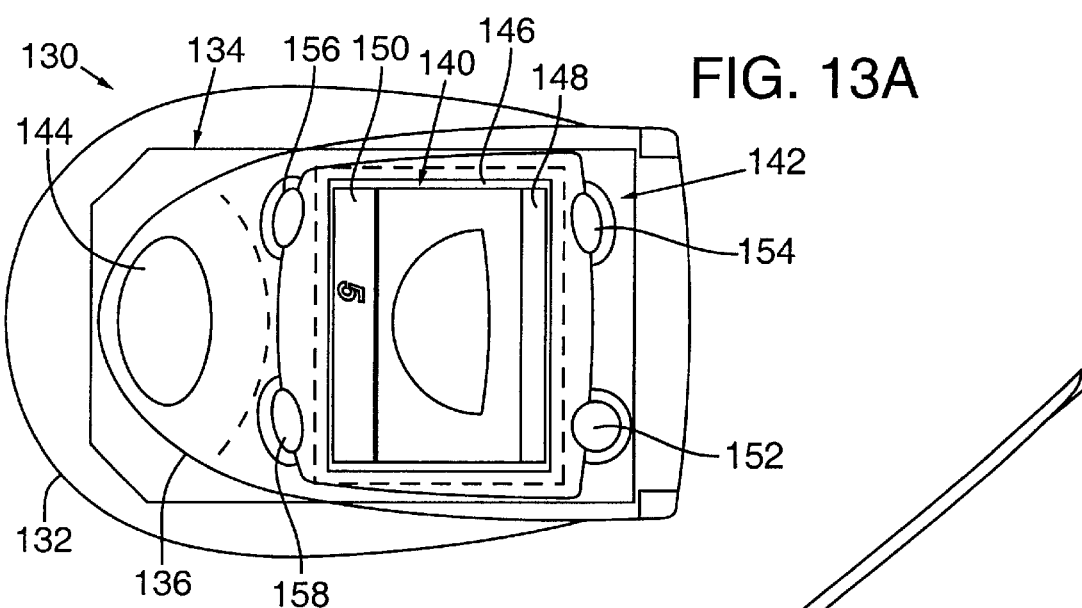
FIGS. 13A–13D are top, side and cross-sectional views of the embodiment of the training unit shown in FIG. 7.
Figure 13B:
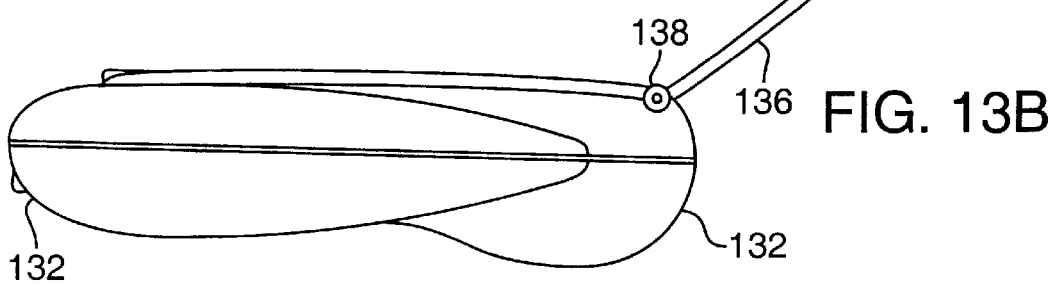
Figure 13C:
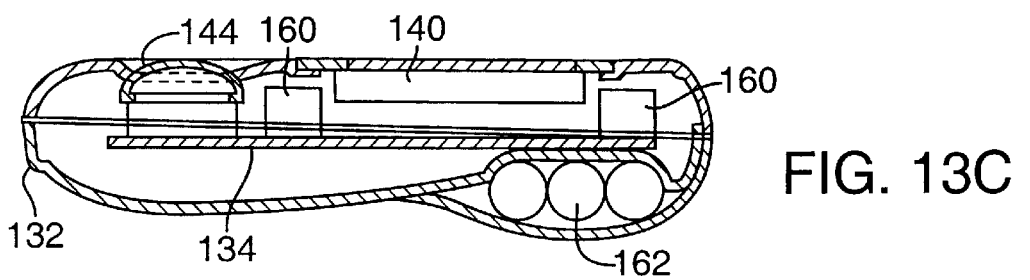

FIG. 13C shows a cross-sectional view of the training unit 130. In this embodiment, the display 140 is mounted to the outer case 132 and is spaced apart from the printed circuit board (PCB) 134. Switching supplies 160 are mounted to the PCB 134 and provide backlighting to the display 140. Batteries 162 supply power to the training unit 130.

Figure 13D:
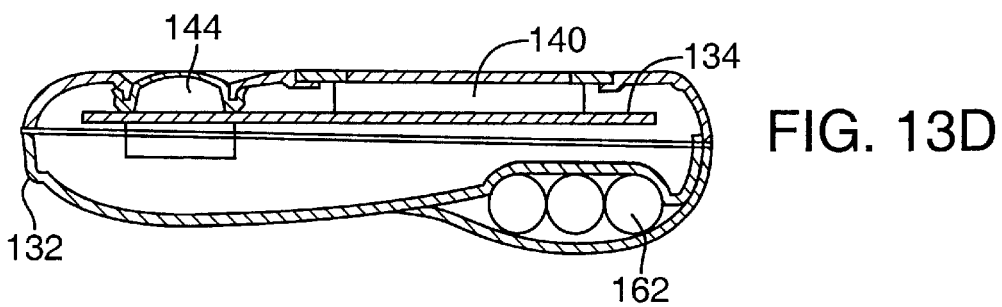

FIG. 13D shows another embodiment of the present invention with the PCB 134 mounted directly to and supported by the display 140. In this embodiment, the display is not backlit so switching supplies are not needed. Although FIGS. 13C and 13D show several different alternatives to packaging for the training unit 130, the packaging is not critical to the invention and alternative designs may be used.

Figure 7:
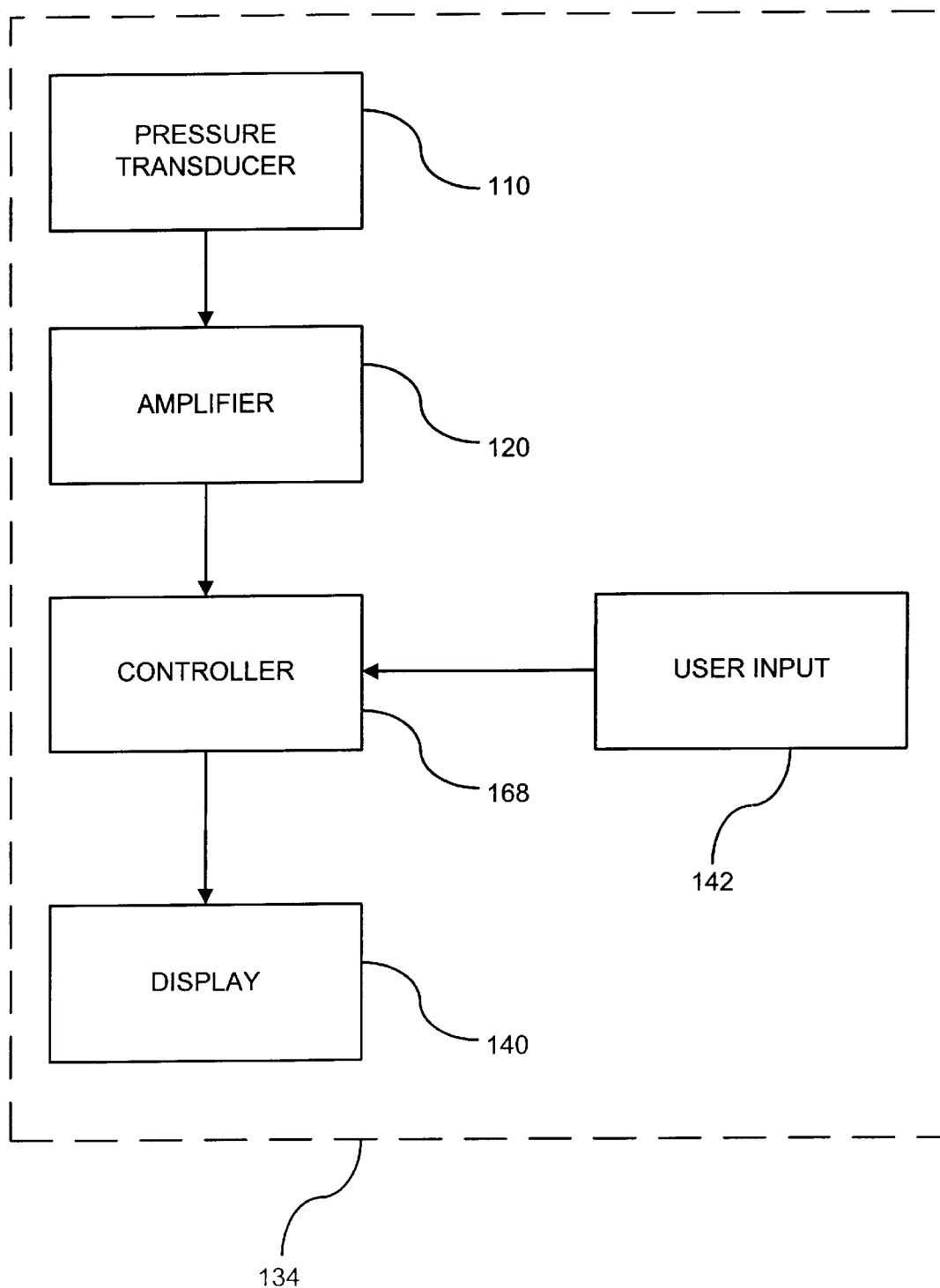
FIG. 7 is a block diagram of electrical components for a training unit according to another embodiment of the present invention, which guides a user through an exercise routine of the pelvic floor muscles.

FIG. 7 illustrates components mounted to the PCB 134. A sensor or pressure transducer 110 is similar to the transducer shown in relation to FIGS. 3 and 4 and is manufactured by Sensyn, Part No. SCCO5D. The amplifier 120 is also similar to that already described in connection with FIG. 4. The controller 168 is a 68-pin integrated circuit designed by MicroChip Corporation, Part No. PIC16LC924. Other amplifier configurations, microcontrollers or microprocessors may, of course, be used. User input 142 includes the user input buttons, such as the power on/off button 152, the strength button 154, the solo button 156, and the time button 158. Other user input devices may be used in place of the buttons. The user input 142 is coupled to input ports on the controller and can be latched, polled, or detected through interrupt control. Those skilled in the art will readily appreciate other techniques can be used for receiving input data from a user input. Regardless of the technique used, the controller 168 recognizes when a user is activating one of the user input buttons. The display 140 is coupled to the controller 168 allowing the controller to guide the user through an exercise routine using information displayed on display 140. The displayed information is based on user input received from the user input buttons.

FIG. 8 shows the functionality of the electronic training unit 130 after the power on/off button 152 is activated. Even when the training unit 130 is switched off, power is supplied to the controller 168 by batteries 162 (FIG. 13C). When off, the controller 168 is in a low-power or sleep mode that allows previous operating parameters, such as strength and time settings, to be stored for later retrieval. During this sleep mode, the controller 168 deactivates its own clock to conserve energy. Upon activation by the user of the power on/off button 152 (step 174), the controller 168 exits the sleep mode, resets other components on the PCB, provides excitation voltage to the transducer 110 and begins executing internally-stored instructions (step 176). Additionally, excitation voltage is applied to the transducer. When the power-on sequence is completed, the controller 168 automatically switches the training unit 130 to a set-up mode (step 178). In the setup mode, the strength and time operating parameters may be adjusted by the user by using the strength button 154 and time button 158.

Turning briefly to FIG. 12E, the strength and time buttons are described more thoroughly with reference to the display 140. The pressure indicator portion 146 of the display 140 shows multiple, semicircular or concentric arcuate pressure-indicator segments that indicate probe pressure induced by the contraction of the user's pelvic floor muscles. The stronger the contraction of the pelvic floor muscles, the greater the number of semicircular segments are displayed. A maximum pressure under the current pressure scale is indicated with a solid circle located at the center of the semicircular segments. The strength button 154 allows the user to change the pressure scale (i.e., change the maximum pressure) of the pressue indicator portion 146. Thus, the training unit 130 is adaptable to users having pelvic floor muscles of varying strengths. FIG. 12E shows the strength setting set to 1 in the strength portion 148 of the display. To change the strength setting, the user presses the strength button 154 until the desired setting is displayed. The time buttons are used to adjust the exercise routine by changing the length of flex or relaxation cycles.

Returning to FIG. 8, steps 180 and 182 show a pump mode wherein the subject uses the pump bladder 144 (FIG. 13.) to inflate the probe 50. During these steps, the user is directed to inflate the probe 50 through a "pump" indication on the display 140. As the probe is inflated, the controller 168 monitors the probe pressure to determine if it is at a sufficient pressure for exercising. If the probe is below the desired pressure, step 182 is answered in the negative and the controller 168 continues to direct the user to pump the bladder 144. When the probe is sufficiently inflated, step 182 is satisfied and the controller automatically enters a ready period (184). Thus, the controller 168 automatically detects when sufficient pressure is in the probe 50 and begins the ready period in response thereto. Additionally, the controller stores the value of the pressure during the ready period. This pressure is called the at-rest pressure because the user has not started muscle contractions.

FIGS. 11A–E show the display 140 as the controller 168 executes steps 180 and 182. On the pressure indicator portion 146 of the display 140, the word "pump" is displayed to direct the user to continue pressing the pump bladder 144. In FIG. 11A, when the probe 50 is at a low pressure, a single vertical line is displayed to indicate the at-rest pressure in the probe 50. As the user continues to press the pump bladder 144, the pressure indicator portion 146 of the display continuously displays a corresponding increase in probe pressure by adding additional vertical lines and other graphics, as shown in FIG. 11B through FIG. 11E. The display signals that the maximum pressure has been reached when the solid circle appears at the center of the display. Subsequently, as shown in FIG. 11F, when the controller has detected sufficient pressure in probe 50 to begin the exercise routine, the word "ready" appears indicating the controller has switched to the ready period (FIG. 8, step 184).

During the ready period (step 184), the controller waits a predetermined period of time to allow the user to prepare for the exercise routine. The controller decrements a count on the timing portion 150 of the display 140 so the user knows exactly when the exercise routine is to begin. FIGS. 12A–C show the display 140 during the ready period. A timing element 186 on the timing portion 150 sequentially counts from a predetermined number, such as five seconds (as shown in the bottom margin of display 140 in FIG. 12A), to one second, as shown in the bottom margin of the display 140 in FIG. 12C. FIG. 12B also shows an intermediate screen with three seconds left in the timing period.

Returning to FIG. 8, in step 188 the controller 168 automatically checks to ensure that the inflation pressure in the probe 50 does not exceed a predetermined threshold. If the probe exceeds a recommended pressure, a warning is given to the user (step 190). The controller 168 then automatically returns the to the set-up mode initialization screen executed at step 178. If at step 188 the probe pressure is at an acceptable pressure, the controller automatically enters the training unit 130 into a workout phase, shown in FIG. 9.

FIG. 9 shows that the training unit 130 has four workout modes 192, 194, 196 and 198. Two of the modes, 192 and 194, utilize the probe 50 (called probe mode). Two of the modes 196 and 198 do not utilize the probe (called solo mode). When the probe is not utilized, the user is directed by the training unit 130 when to flex and relax muscles so as to guide the user through a prescribed exercise routine. The solo mode allows the user to exercise their pelvic floor muscles in a public area.

In step 199, the controller determines whether the training unit is in solo mode. If the training unit is in probe mode, the controller 168 determines which of two probe modes the user selected. For purposes of this application, the two probe modes 192, 194 are called probe wink mode and probe work mode, respectively.

In step 200, the controller 168 determines whether probe wink mode 192 is selected. In probe wink mode, the user flexes the pelvic floor muscles (after insertion and inflation of the probe) while the pressure indicator portion 146 of the display 140 displays the associated pressure increase due to the contraction of the user's pelvic floor muscles. In step 202, the controller 168 executes wink mode which is described further below in relation to FIG. 10. A predetermined timer is also set and continuously checked (step 204). If the timer has not expired, the controller 168 continues to execute the wink mode (step 202). However, after the predetermined time period has expired, the controller 168 returns to step 176 (FIG. 8) and enters a sleep mode. Thus, for example, the probe wink mode 192 helps the user to flex the pelvic floor muscles by indicating when they are contracting them, and then subsequently relaxing them, for a pre-set time period (for example two to five minutes) before returning to a sleep mode. In an alternative embodiment of the probe wink mode, the training unit 130 alternates between contraction and relaxation cycles in very quick intervals, such as every 2 seconds.

If in step 200 the controller determines the wink mode 192 is not selected, then the controller enters a probe work mode 194. The probe work mode 194 requires the user to choose different time settings by depressing the time button 158 during the setup mode initialization 178. For example, a time setting of five or ten seconds may be used. The time setting controls the time between alternating flex cycles (where a flex cycle is a contraction). In step 206, the probe work mode is executed, as is further described in relation to FIG. 10. A predetermined timer is also set and continuously checked (step 208). If the timer has not expired, then the controller continues to execute the probe work mode (step 206). However, after the predetermined time period has expired, the controller 168 returns to step 176 (FIG. 8) and enters a sleep mode.

One skilled in the art will recognize that the function of solo modes 196 and 198 are similar to the probe modes 192 and 194, as described above. The differences between solo and probe modes is more clearly understood in relation to FIG. 10.

Figure 10A:
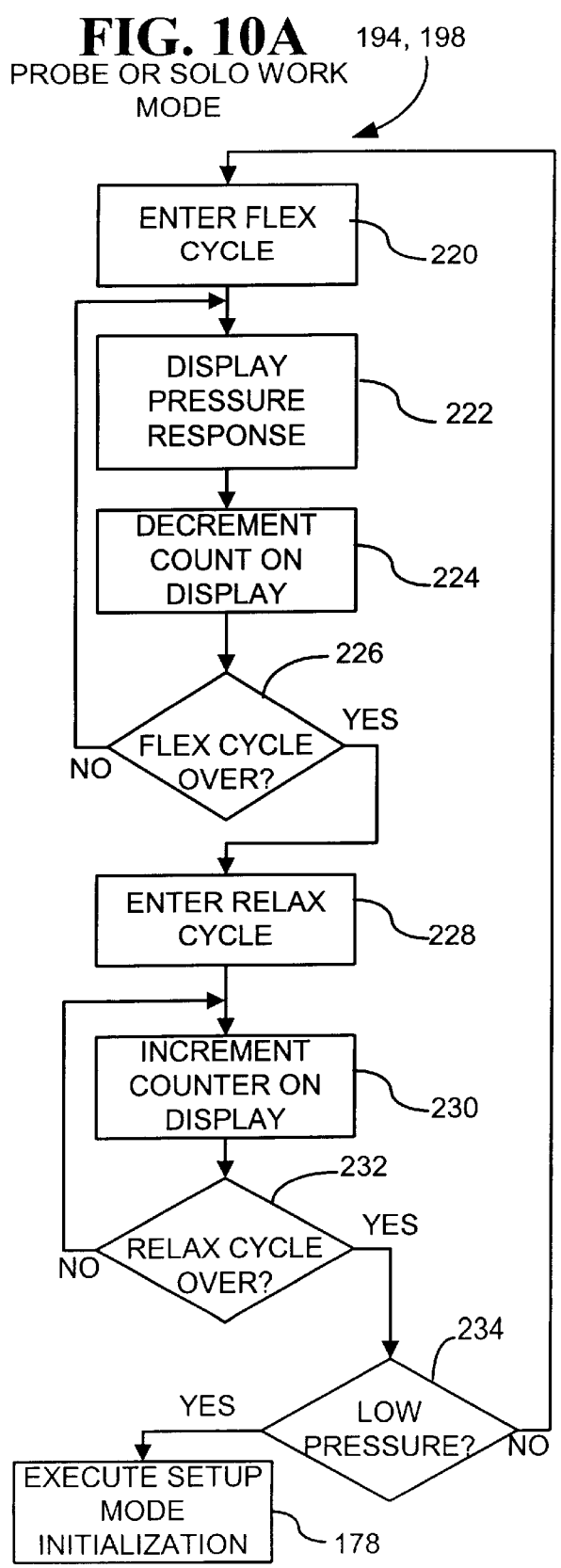
FIGS. 10A–10B are detailed flowcharts of steps taken by the training unit of FIG. 7 during a workout phase.
Figure 10B:
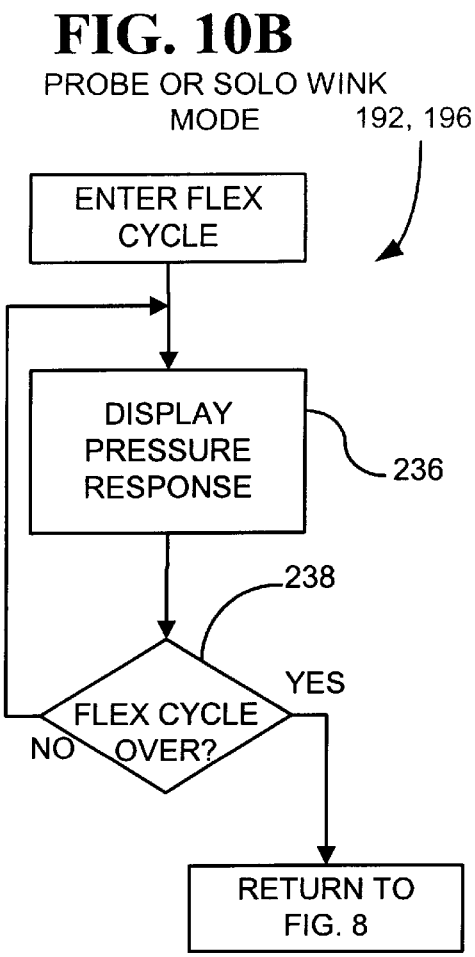

FIG. 10 shows the four workout modes 192, 194, 196 and 198 in greater detail. First turning to modes 194 and 198 shown in FIG. 10A, the controller 168 enters a flex cycle (step 220). During the flex cycle, the display 140 displays the word "flex" on the pressure indicator portion 146 of the display. Additionally, the pressure indicator portion 146 shows concentric semicircles that indicate the pressure increase over the at-rest pressure. This pressure increase is due to squeezing of the probe 50 when the user contracts the pelvic floor muscles. Unlike previous prior art displays that show the total pressure in the probe 50, the pressure indicator portion 146 of the present invention only shows an increase in pressure due to contraction of the pelvic floor muscles. To display only the contraction pressure, the controller stores the at-rest pressure obtained during the ready period prior to contraction by the user. The controller then obtains the total pressure during exercising. The at-rest pressure is subtracted from the total pressure to obtain the contraction pressure resulting from the subject's contraction of the pelvic floor muscles. As indicated in FIG. 12E, the more pressure the user places on the probe 50 due to the muscle contractions, the more concentric semicircles are displayed. If the user squeezes sufficiently to register a maximum pressure in the probe 50, the display shows multiple concentric semicircles and a solid-filled circle at the center (FIG. 12F). Each semicircle in the pressure indicator portion 146 of the display 140 represents a pressure threshold that has been exceeded.

The display shown in FIG. 12 is particularly advantageous for the biofeedback device of the present invention, where contraction of the pelvic floor muscles around the probe 50 constitutes a tightening of the muscles around the probe. As muscles tighten, they reduce in size. The series of nested semi-circles on the display in FIG. 12 therefore have an intuitive physiological correspondence to the anatomic act being performed. As the muscles tighten to a smaller area, the semi-circles correspondingly have smaller diameters. The solid dot at the center of the display also corresponds to the probe 50 around which the muscles are tightening. This intuitive display helps many users overcome the inherent difficulty of coordinating contraction of an unfamiliar muscle group around the probe.

The display can take many other forms while still conveying this intuitive physiological correspondence to the tightening of the pelvic floor muscles. For example, any nested series of regular patterns converging to a common center would achieve a similar effect. Nested half-rectangles or arcuate concentric or parallel curves are examples of alternative patterns that would be suitable. A series of concentric circles or ovals can also be used instead of the half circles shown in the embodiment of FIG. 12. The converging nested patterns could also be used without the central solid circle.

Returning to FIG. 10, the pressure response is displayed to the user during the workout modes 194 and 198 (step 222). In the probe workout mode, the displayed pressure response is associated with the actual pressure on the probe 50. In the solo workout mode 198, the pressure response shown is a fictitious response generated by the controller 168 to indicate an ideal pressure response. In step 224, a countdown is displayed on the timing portion 150 of the display 140 to indicate the amount of time remaining in the flex cycle (see FIGS. 12D and 12E). In step 226, the controller 168 determines whether the flex cycle is over. If the cycle is not over, steps 222 and 224 are executed again. If, however, the flex cycle is over based upon reaching a predetermined time limit, the controller automatically enters a relaxation cycle (step 228). The controller displays the word "relax" on the pressure indicator portion 146 of the display to direct the user to relax the pelvic floor muscles. A count on the timing portion 150 of the display is incremented or decremented to indicate to the user the amount of time remaining in the relax cycle (step 230). In step 232, the controller 168 determines whether the relaxation cycle is over. If it is not, the controller continues to increment or decrement the count on the timing portion of the display. When the relaxation cycle is over, the controller 168 automatically checks to determine if the pressure in the probe 50 is below a predetermined threshold (step 234). If the pressure is low, the controller automatically enters the setup mode (178—FIG. 8) to allow the user to increase pressure in the probe by using bladder 144. If the probe pressure is acceptable in step 234, then the controller again enters the flex cycle 220. The flex and relaxation cycles thereby alternate for predetermined periods of time.

The probe and solo wink modes 192 and 196 help the user to flex for a predetermined period of time. During this period, the actual pressure response is displayed in probe wink mode (step 236) and a simulated pressure response is displayed in solo wink mode. In step 238, the controller 168 determines whether the flex cycle is over. During the probe wink mode, a relax cycle is not entered. However in the solo wink mode a relax cycle is entered. The controller 168 then returns to the sleep mode (step 176—FIG. 8). Alternatively, the controller can alternate between flex and relaxation cycles during the wink modes.

The training unit 130 can also be provided with a data port for connecting the device to an external conventional personal computer. A serial data communications port can utilize an infrared optical coupling to implement an asynchronous serial data communication port. This transmit only port allows external monitoring and verification of sensor transducer pressure. It can also be used to monitor compliance with a prescribed exercise regimen, and can even be downloaded to a remote site for evaluation by a health care provider. To maximize battery life, the port will transmit transducer pressure at one minute intervals only if the solo button is held in the depressed condition while the unit is switched on. When the unit is turned off, data transmission is disabled.

In operation, either of probes 52, 54 are inserted into the orifice of a user and inflated to a user-determined level. Thereafter, the user may, by successively flexing and relaxing the pelvic floor muscles adjacent and surrounding the probe, observe over display 76 or display 140, representations of the pressures exerted on the probe and detected by transducer 110.

Describing the operation of training unit 130 more specifically, once a probe has been inserted into a desired orifice (such as a vagina, anus or rectum), it may be inflated via pump bladder 74 or bladder 144 by the user's repetitive actuation thereof, which causes air to flow through conduit 66 and into the probe via apertures 62 in tubular structure 60. The elastic skin of the probe expands due to the increase in air pressure, filling the user's orifice and exerting a slight positive pressure on the surrounding muscles. Switch 80 may be set by the user to one of three strength settings for achieving the different exercise levels described above. Alternatively, in the embodiment of FIG. 13, the strength button 154 can be used.

Figure 6:
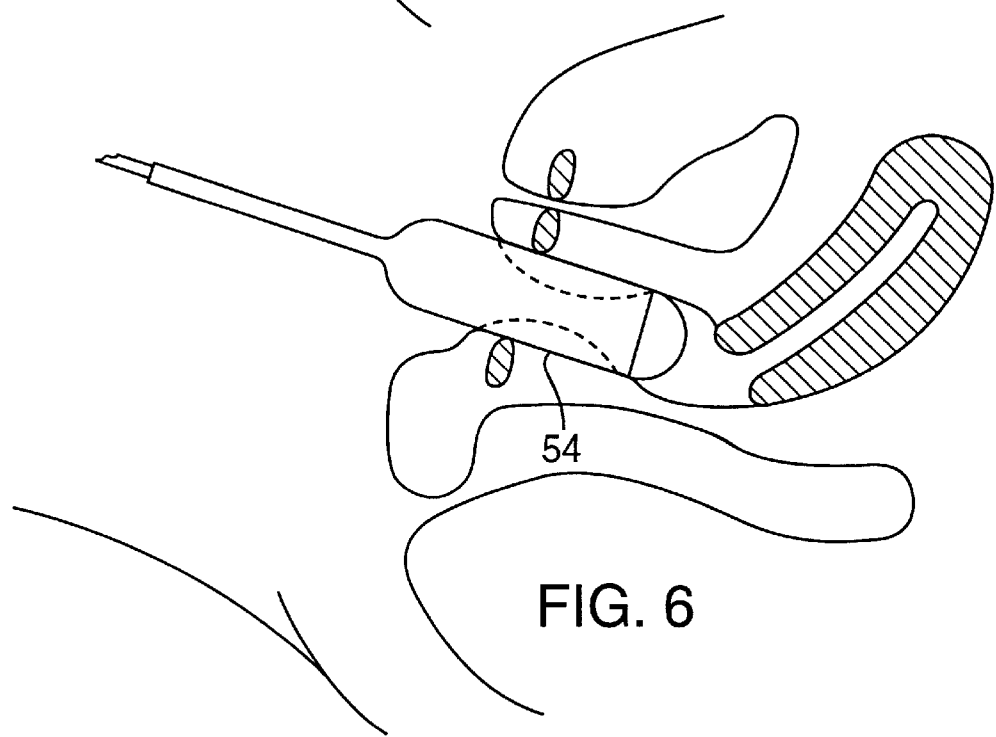
FIG. 6 is a schematic cross-sectional view showing the vaginal probe in use in a female subject.

FIGS. 5 and 6 depict probes 52, 54, inserted respectively into the rectum of a male, and a vagina. Sphincter and pelvic floor muscles may thereafter be repetitively exercised by the recipient user, for improved urinary and bowel control. More specifically, as the user flexes the surrounding muscles, the central portion of each probe is compressed (as shown in dashed lines), moving air out of the probe, through the conduit, and into cavity 112 in manifold 82, whereupon transducer 110 detects the differential pressure change, produces a representative signal thereof which is conveyed after amplification to the display/driver described above. By observing the display on control unit 70 or training unit 130, the user is able to ascertain valuable biofeedback information relative to the flexure and relaxation of the muscles. More specifically, with respect to training unit 130 the pressure response is displayed on display 140. Alternatively, with respect to display 76, the reader will appreciate that biofeedback information relative to the user's muscle flexure and relaxation is provided in the form of plural LEDs 78, which are signal-responsive and have a first direction which is serially-progressing, LED-by-LED, corresponding to successive on-states. During such serial progression (which corresponds to progressive contraction of the user's muscles against the probe), the lighted length of the bar-graph increases in direct proportion to such sensed pressures. Correspondingly, when the user relaxes the muscles adjacent and surrounding the probe, the series of LEDs just described serially digress in a second direction, LED-by-LED, which direction is opposite to the first direction.

If, during a relax period, sensor pressure fails to drop below a predefined threshold level during the first half of the period, the "relax" indicator will alternate between on and off until completion of the relax period. The predefined threshold pressure may be, for example, one-half the selected workout pressure.

Having described and illustrated the principles of our invention with reference to several preferred embodiments, it will be apparent that these embodiments can be modified in arrangement and detail without departing from the principles of the invention.

Although the display is shown in the form of LEDs and a LCD, other forms of displays, such as those developed in the future, can easily be substituted. Additionally, although the display is shown with a timing portion, a pressure indicator portion, and a strength portion, the display can have any desired layout. One or more portions of the display may be omitted based on the application.

Also, although particular inflatable probe is shown, any pneumatic or non-pneumatic probe may be used. Other means of inflating the probe, besides the pump bladder, can be used.

In view of the wide variety of embodiments to which the principles of our invention can be applied, it should be apparent that the detailed embodiments are illustrative only and should not be taken as limiting the scope of my invention. Rather, we claim as our invention and all such modifications as may come within the scope of the following claims and equivalence thereto.

We claim:

1. A method for assisting a user through an exercise routine of the user's pelvic floor muscles, comprising:
   inserting an inflatable probe into an orifice of the user;
   detecting a pressure applied to the probe by the user's pelvic floor muscles;
   displaying a pressure indicator associated with probe pressure on a display, the display having a graphical representation of muscles surrounding the probe; and
   modifying the display in response to changes in probe pressure such that there is a physiological correspondence between the graphical representation of muscles on the display and the muscle contraction by the user.

2. The method of claim 1 further including changing a pressure scale associated with the pressure indicator on the display in response to user input.

3. The method of claim 1 further including displaying, on the display, instructions directing the user to manually increase pressure in the inflatable probe.

4. The method of claim 3 further including automatically entering a ready period in response to detection of sufficient pressure in the inflatable probe, the ready period indicating that the user should be ready to begin the exercise routine.

5. The method of claim 1 further including determining an at-rest pressure prior to muscle contraction of the user and wherein displaying a pressure indicator associated with probe pressure on a display includes displaying only a pressure increase over the at-rest pressure.

6. The method of claim 1 further including storing an at-rest pressure in the probe prior to muscle contraction by the user, determining total pressure in the probe, and subtracting the at-rest pressure from the total pressure to obtain a pressure increase caused by the user's muscle contraction.

7. The method of claim 1 wherein displaying a pressure indicator associated with probe pressure on a display includes displaying concentric geometric patterns and wherein each concentric geometric pattern represents a different pressure threshold associated with pressure in the probe.

8. The method of claim 1 wherein displaying a pressure indicator associated with probe pressure on a display includes displaying concentric curvilinear lines and wherein curvilinear lines with a smaller diameter are displayed in response to increased probe pressure.

9. The method of claim 1 further including automatically checking pressure in the probe while in an exercise mode of operation and if the pressure is below a predetermined threshold, requesting the user to manually increase pressure.

10. The method of claim 1 further including storing information associated with the exercise routine and providing a data port for downloading the information to an external computer.

11. A method for assisting a user through an exercise routine of the user's pelvic floor muscles, comprising:
    inserting an inflatable probe into an orifice of the user;
    detecting a pressure applied to the probe by the user's pelvic floor muscles;
    displaying, on a display, a pressure indicator associated with pressure in the inflatable probe, the display having a graphical representation of muscles surrounding the probe including concentric geometric patterns, wherein each concentric geometric pattern represents a different pressure threshold associated with pressure in the probe.

12. The method of claim 11 further including changing a pressure scale associated with the pressure indicator on the display in response to user input.

13. The method of claim 11 further including displaying, on the display, instructions directing the user to manually increase pressure in the inflatable probe.

14. The method of claim 13 further including automatically entering a ready period in response to detection of sufficient pressure in the inflatable probe, the ready period indicating that the user should be ready to begin the exercise routine.

15. The method of claim 11 further including determining an at-rest pressure prior to muscle contraction of the user and wherein displaying a pressure indicator associated with probe pressure on a display includes displaying only a pressure increase over the at-rest pressure.

16. The method of claim 11 further including storing an at-rest pressure in the probe prior to muscle contraction by the user, determining total pressure in the probe, and subtracting the at-rest pressure from the total pressure to obtain the pressure increase caused by the user's muscle contraction.

17. The method of claim 11 wherein displaying concentric geometric patterns includes displaying concentric curvilinear lines having predetermined diameters and wherein the curvilinear lines with a smaller diameter are displayed in response to increased probe pressure.

18. The method of claim 11 further including automatically checking pressure in the probe while in an exercise mode of operation and if the pressure is below a predetermined threshold, requesting the user to manually increase pressure.

19. The method of claim 11 further including storing information associated with the exercise routine and providing a data port for downloading the information to an external computer.

20. The method of claim 11 further including displaying alternating flexing and relaxation cycles for guiding the user through an exercise routine of the pelvic floor muscles wherein during the flexing cycle the display directs the user to flex the pelvic floor muscles and wherein during the relaxation cycle the display directs the user to relax the pelvic floor muscles.

21. The method of claim 11 further including automatically monitoring the pressure in the inflatable probe and terminating the exercise routine when the pressure in the probe is below a desired threshold.

22. The method of claim 11 further including providing a solo mode where in the inflatable probe is disabled and the method further includes displaying a fictitious pressure response to the user during the solo mode.

23. A method for assisting a user through an exercise routine of the user's pelvic floor muscles, comprising:

inserting an inflatable probe into an orifice of the user;

detecting a pressure applied to the probe by the user's pelvic floor muscles;

displaying, on a display, pressure information associated with the pressure detected in the probe caused by the flexing and relaxation of the user's pelvic floor muscles;

monitoring the pressure in the probe an d automatically terminating the exercise routine when the pressure in the probe is below a desired threshold.

24. The method of claim 23 wherein displaying pressure information includes displaying a pressure indicator associated with pressure in the inflatable probe, the pressure indicator including a graphical representation of muscles surrounding the probe such that there is a physiological correspondence between the graphical representation of muscles on the display and muscle contraction by the user.

\* \* \* \* \*